United States Patent [19]

Riedel et al.

[11] Patent Number: 4,793,003

[45] Date of Patent: Dec. 27, 1988

[54] LIGHT OCCLUSIVE EYE PATCH

[75] Inventors: John E. Riedel, White Bear Lake, Minn.; Jay V. Ihlenfeld, Neuss, Fed. Rep. of Germany

[73] Assignee: Minnesota Mining and Manufacturing Company, St. Paul, Minn.

[21] Appl. No.: 878,995

[22] Filed: Jun. 26, 1986

[51] Int. Cl.$^4$ .............................................. A61F 9/04
[52] U.S. Cl. ........................................ 2/15; 128/858; 128/163; 604/366; 604/371
[58] Field of Search ................. 2/15, 12, 268, 174; 128/132 R, 163

[56] References Cited

U.S. PATENT DOCUMENTS

| | | | |
|---|---|---|---|
| 2,165,668 | 7/1939 | Vaccaro | 2/15 |
| 3,068,863 | 12/1962 | Bowman | 2/15 X |
| 3,092,103 | 6/1963 | Mower | 128/132 |
| 3,908,645 | 9/1975 | Sandvig | 128/97 |
| 4,122,847 | 10/1978 | Craig | 2/15 X |
| 4,599,746 | 7/1986 | Stoner | 2/15 |

FOREIGN PATENT DOCUMENTS 2605275 8/1976 Fed. Rep. of Germany .

*Primary Examiner*—Peter Nerbun
*Attorney, Agent, or Firm*—Donald M. Sell; Walter N. Kirn; Carolyn A. Bates

[57] ABSTRACT

A light-occlusive self adherent eyepatch is disclosed comprising an absorbent pad having a nonadherent lower surface, a thin microporous polymeric film overlying the upper surface of the pad, pressure sensitive adhesive means extending around the periphery of the pad to adhere the patch to the eye socket, and a removable liner protecting the lower surface of the pad and the adhesive prior to use. The polymeric film blocks at least 95 percent of the light of a preselected wavelength impinging on the film, and the overall eyepatch is conformable and moisture vapor permeable.

10 Claims, 1 Drawing Sheet

LIGHT OCCLUSIVE EYE PATCH

FIELD OF THE INVENTION

This invention relates to the field of light occlusive eye patches. More particularly, it relates to light-occlusive eye patches having a pressure sensitive adhesive on the peripherial portion of the patch to adhere the patch to the area of the body around the eye.

BACKGROUND ART

In the United States, strabismus (ambliopia) in children is most often corrected by surgical procedures. Non-surgical alternatives such as occlusive eye patches, fresnel eyeglass lenses, and the like are also available and are the first treatment of choice in Europe. The use of self-adhesive occlusive eye patches is quite common.

In occlusive therapy, an eye patch is applied daily over the nonaffected eye of the child. On average, the patch is worn for two hours each day, longer for older children, shorter for younger children. There is some evidence in the literature to suggest that the efficacy of occlusive therapy is improved if the occlusive patch can be made so as to effectively prevent the passage of light ot the nonaffected eye. The objective of occlusive therapy is to maintain the nonaffected eye (beneath the occlusive patch) immobile while the uncovered affected eye is free to move in response to visual stimuli. It is believed that small amounts of light passing through the occlusive patch to the nonaffected eye stimulate undesireable eye movement, thereby decreasing the efficacy of the treatment.

Criteria for an acceptable self-adhesive occlusive eye patch include the use of a gentle, hypoallergenic adhesive, softness and conformability to the eye socket, breatheability, i.e., moisture vapor and air permeability to reduce the potential for skin damage, and cosmetic appeal. Furthermore, a light occlusive patch should effectively block the passage of ambient light without sacrificing any of the above requirements. Prior to the present invention, a self-adhesive occlusive eye patch having this combination of properties was not available.

A product known as Opticlude ® Orthoptic Eye Patch sold by 3M comprise an adsorbent pad having nonadherent films on its upper and lower surfaces. A layer of skin-tone nonwoven medical tape, i.e., Micropore ® brand tape, overlies the adherent film on the upper surface of the pad and extends beyond the periphery of the pad in all directions to secure the patch to the eye socket. A removable liner protects the pad and adhesive layer prior to use.

Although Opticlude ® patches meet most of the criteria listed above, they effectively block only about 75 percent of the incoming ambient light. Several years ago attempts were made to modify the Opticlude ® product to make it light occlusive. A stiff, black, light-absorbing polyethylene film layer overcoated with a solid resin layer for skin toning was inserted between the nonwoven tape and the adsorbent pad. In field testing, particularly in Germany, these patches reportedly caused skin irritation when worn and/or removed. The source of the irritation appeared to be the stiffness of the black film layer as well as the fact that the black film layer with its skin toned resin overcoat did not have good moisture vapor permeability.

Another product which has attempted to provide light occlusivity is Elastopad-lite occlusive plasters sold in Europe by Beiersdorf. This product is a laminate comprising an adsorbent pad, a layer of black nonwoven material and a layer of porous skin-tone polyvinyl chloride overlying the black nonwoven layer. A piece of skin-toned tape overlies the polyvinyl chloride layer and extends beyond the periphery of the other layers of the patch to adhere the patch to the eye socket. While the Elastopad product is moisture vapor permeable and appears to block virtually all of the ambient light, it is relatively thick, and no sufficiently soft and conformable to insure maximum comfort.

Accordingly, the need still exists for a self-adherent eye patch which is thin, soft, breathable, conformable and confortable to wear, and also blocks virtually all incoming light. The present invention effectively fulfills the aforementioned need.

BRIEF SUMMARY OF THE INVENTION

According to the present invention, there is provided a self-adherent eye patch comprising: an absorbent pad shaped to fit over the eye having a nonadherent lower surface for contacting the eye and an opposing upper surface; a thin microporous polymeric film capable of blocking at least 95 percent of light in a preselected wave length adhered to the upper surface of the absorbent pad and at least coextensive with the pad; pressure sensitive adhesive means adjacent the periphery of the pad for adhering the eye patch to the eye socket; and a removable protective liner covering the nonadherent lower surface of the pad and the exposed portion of the pressure sensitive adhesive prior to use. The eye patch must have a moisture vapor permeability of at least 600 grams per square meter per 24 hours throughout and have a conformability value less than 800 grams, and preferrably less than 600 grams, when tested according to the test methods set forth herein below.

In the preferred embodiment of the eye patch of the invention, the light occlusive microporous polymeric film extends beyond the periphery of the absorbent pad in all directions and is coated on its lower surface with a pressure sensitive adhesive. The adhesive serves to adhere the film to the pad and to adhere the patch to the eye socket. This embodiment is especially preferred because it comprises a minimum of layers and is light occlusive throughout its total area, even the area extending beyond the periphery of the patch.

In another embodiment of the eye patch of the invention, the light occlusive microporous polymeric film is coextensive with the pad and a layer of tape, such as Micropore ® brand tape, overlies the polymeric film and extends beyond the periphery of the film to adhere the eye patch to the eye socket. This embodiment is less preferred because it is not light-occlusive in the area around the periphery of the pad.

The preferred light occlusive microporous polymeric film is high density porous polyethylene which has been pigmented with a skin-toned pigment.

A further aspect of the invention relates to a method of treating an eye defect or tramatized eye which benefits from light occlusive therapy by covering the eye with the self-adherent eye patch described above.

The self adherent eye patch of the present inventon provides an eye patch which is thin, conformable, breathable throughout its entire area, cosmetically appealling, and capable of blocking virtually all of the ambient light throughout its entire area, if desired.

DETAILED DESCRIPTION OF THE DRAWINGS

The invention is further illustrated by reference to the accompanying drawings wherein like reference numerals refer to like elements FIG. 1 is a top plan view of the eyepatch of the invention;

Figure 1:
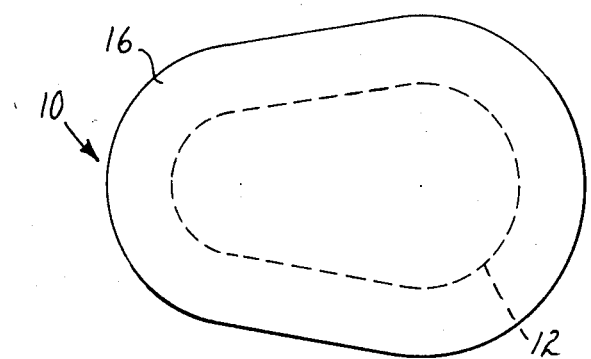
Figure 2:
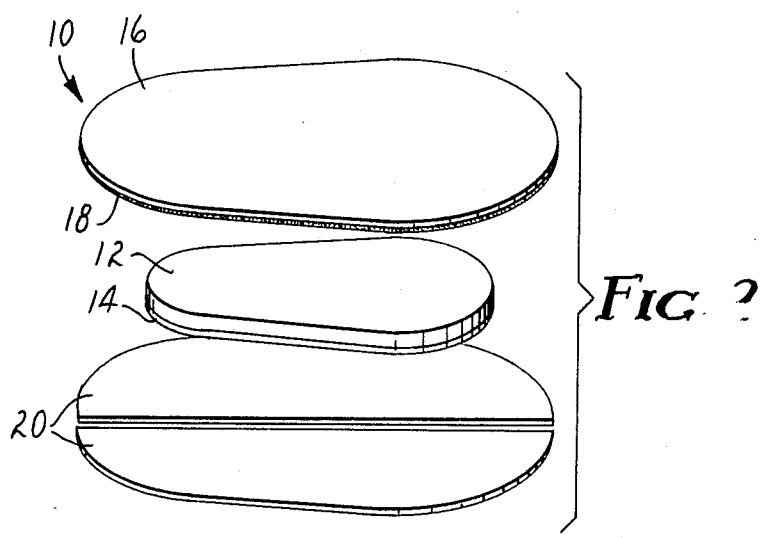
FIG. 2 is an exploded perspective view of one embodiment of the eyepatch.

Referring now to FIGS. 1 and 2, there is shown in eyepatch 10 comprising an absorbent pad 12 shaped to fit over the eye having a nonadherent surface 14 on its underside for placing in contact with the eye. The upper surface of the absorbent pad 12 is adhered to a microporous pigmented polymeric film 16 by a layer of pressure sensitive adhesive 18. Film 16 must be capable of blocking at least 95 percent of the ambient light. Film 16 and adhesive 18 on the underside thereof extend beyond the periphery of the absorbent pad 12 in all directions exposing enough adhesive 18 to securely adhere the eyepatch to the eye socket. A removable protective liner 20 covers the nonadherent underside of absorbent pad 12 and the exposed pressure sensitive adhesive 18 prior to use.

Figure 3:
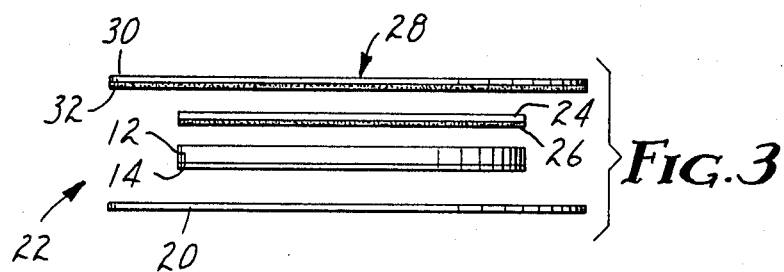
FIG. 3 is an exploded side elevational view of a second embodiment of the eyepatch.

Referring now to the embodiment of FIG. 3, eyepatch 22 comprises absorbent pad 12 having a nonadherent surface 14 on its underside for placing in contact with the eye. The pad and nonadherent surface are identical to those illustrated in FIG. 2. Eyepatch 22 further comprises a microporous pigmented polymeric film 24 having a layer of pressure sensitive adhesive 26 on its under surface to adhere film 24 to the top surface of pad 12. Film 24 and adhesive 26 are identical in composition to film 16 and adhesive 18 of the embodiment of FIG. 2, the only difference being in overall dimensions. Film 24 and adhesive 26 are dimensioned so as to be coextensive with pad 12. They do not extend beyond the periphery of pad 12. Over the top surface of film 24 is adhered a breathable tape 28 comprising backing 30 and a pressure sensitive adhesive 32 on the undersurface thereof. Tape 28 extends beyond the periphery on the pad 12 and film 24 in all directions to provide sufficient exposed adhesive 32 to securely adhere the eyepatch to the eye socket.

As in FIG. 2, removable protective liner 20 covers the underside of absorbent pad 12 and the exposed adhesive 32 prior to use.

The absorbent pad 12 provides cushioning and protection to the eye as well as fluid absorbency, and may comprise any of the accepted absorbent materials for surgical dressings, e.g., cotton, rayon, cellulosic batts, etc. The nonadherent surface 14 on the underside of the pad 12 prevents the pad from sticking to the eye and lint from the pad entering the eye. The nonadherent surface may be provided by any of the conventional methods known in the dressing art for preventing a dressing from sticking to a wound, a need not involve a separate layer of material. Preferably, the absorbent pad 12 and nonadherent surface 14 are constructed as described in U.S. Pat. No. 3,285,245 by heat bonding thermoplastic polymeric fibers or film such as polyethylene to the surface of a nonwoven web. The thermoplastic polymeric fibers or film melt and coalesce to form a discontinuous naturally porous film. The preferred absorbent pad 12 of this type comprises a needle-tacked rayon web similar to the pad used in the current 3M Opticlude ® product except the polyethylene nonadherent film covers only the lower surface of the pad which contacts the eye.

Microporous polymeric film 16 (film 24 of FIG. 3) provides light occlusivity to the eye patch.

Light occlusivity can be obtained by adding suitable non-toxic dyes or pigments to the polymer matrix or by coating one side of the film with a light absorbing paint or dye. The preferred method is by adding a pigment or mixture of pigments to the polymer matrix.

The film must also be moisture vapor permeable to the extent necessary to provide an overall moisture vapor permeability to the eyepatch of at least 600 grams per square meter per 24 hours. The film must also be relatively thin, i.e., in the range of about 0.001 to 0.008 inch, soft and flexible so as to provide the eyepatch with an overall conformability value of less than 800 grams in the method described below. Examples of films which can be rendered sufficiently light occlusive by the addition of dyes or pigments, yet remain acceptably conformable and moisture vapor permeable include microporous polytetrafluoroethylene, porous polyurethane made according to U.S. Pat. No. 3,870,593, and the porous thermoplastic polymeric films described in U.S. Pat. No. 4,538,256. The later films at a thickness of about 0.002 inch are preferred, especially those formed from high density polyethylene.

Pigments which can be used to render the film light occlusive are preferably fine powders which can be dispersed in the polymer matrix and do not interfere with the extrusion of the polymer matrix into thin films. The preferred pigments are those which produce a skin-toned film. A mixture of black, red and yellow pigments has been found useful in producing a skin-toned color which is stable through the extrusion process. If the pigment used results in a film which is too dark to be cosmetically acceptable, it may be desirable to include a skin-toned cover-up layer. The pigment is generally present in the range of 3 to 5 weight percent of the solids in the polymer matrix.

In most cases, the pigmented film will block transmission of light in all wave lengths, however, if desired for specific pruposes, it may be possible to construct the film so that light of a specific wave length, e.g., ultraviolet light, is blocked but some light in other wave lengths, e.g., visible light, is transmitted.

The adhesive used to provide adhesive 18 (and adhesive 32 of FIGS. 2 and 3) may be any pressure sensitive adhesive commonly used on skin which is non-irritating and has sufficient moisture vapor permeability to insure that the minimum moisture permeability requirements of the overall eyepatch are met. Preferred adhesives are the acrylate polymers described in U.S. Pat. No. 2,884,126 (Reissue No. 24,906).

In the embodiment of FIG. 3, adhesive 26 which secures film 24 to the pad 12 may be different from the adhesive 32 which adheres the patch to the skin. It must, however, have sufficient moisture vapor permeability to ensure the minimum moisture vapor permeability requirements of the eyepatch are met. In some cases, adhesive 32 may be omitted if other means such as heat sealing are used to attach film 24 to pad 12. However, it has been found that with the preferred pigmented porous polyethylene films referred to above, heat sealing damages the film and the use of a pressure sensitive adhesive is the preferred method of laminating these two elements.

In use, the protective liner 20 is stripped from the eyepatch, and the eyepatch is applied over the eye with the absorbent pad 20 in contact with the eye and the adhesive portion of the eyepatch adhered securely to the portion of the face surrounding the eye.

In addition to treating strabismus, the light occlusive eyepatch of the invention may be used in the treatment of eye trauma wherein eye movement is painful or retards healing. Preventing light from entering the eye may help prevent undesirable eye movement. It is also possible to construct the eyepatch to selectively occlude light of certain wave lengths while transmitting some visible light. A UV absorbing patch would be useful for protecting the eyes of small infants undergoing UV therapy or the eyes of people receiving UV radiation, as in commercial tanning studies.

Test Methods

The test methods used to measure moisture vapor permeability, air porosity, conformability and light occlusivity of the eye patches of the invention are set forth below.

Moisture Vapor Permeability

A modified Payne cup method is used. The method comprises the following steps:

(1) A 1⅜ inch (35 mm) diameter sample of material to be tested containing no perforations is cut.

(2) The sample is centered between the adhesive surfaces of two foil adhesive rings, each having a one inch (2.54 cm) diameter hole. The holes of each ring are carefully alligned. Finger pressure is used to form a foil/sample/foil assembly that is flat, wrinkle-free and has no void areas in the exposed sample.

(3) A 4 ounce glass jar is filled half full of distilled water. The jar is fitted with a screw on cap having a 1.50 inch diameter hole in the center thereof and with a 1.75 inch diameter rubber washer having a 1.12 inch diameter hole in its center.

(4) The rubber washer is placed on the lip of the jar and the foil/sample assembly is placed on the rubber washer. The lid is then screwed loosely on the jar.

(5) The assembly is placed in a chamber at 100° F. (38° C.) and 20 percent relative humidity for four hours.

(6) The cap is tightened inside the chamber so the sample material is level with the cap (no bulging) and the rubber washer is in proper seating position.

(7) The assembly is removed from the chamber and weighed immediately to the nearest 0.01 gram (initial weight $-W_1$).

(8) The assembly is returned to the chamber for at least 18 additional hours.

(9) The assembly is removed from the chamber and weighed immediately to the nearest 0.01 gram (final weight $-W_2$).

(10) The water vapor transmission in grams of water vapor transmitted per square meter of sample area in 24 hours is calculated according to the following formula:

$$MVT = \frac{(W_1 - W_2) 4.74 \times 10^4}{T \text{ (hours)}}$$

$W_1$ = initial weight (grams)
$W_2$ = final weight (grams)
$T$ = time (hours)

When a ½ inch sample is tested, the formula is changed to the following:

$$MVT = \frac{(W_1 - W_2) 1.9 \times 10^5}{T \text{ (hours)}}$$

(12) Three samples of each material should be run and the average taken.

Conformability

The conformability (i.e., softness, drape, etc.) of the eyepatch is measured according to INDA Standard Test IST 90-75 (R77) Ring and Rod method, modified to accomodate a smaller sample. Only the center pad portion of the eyepatch (not the adhesive-coated tape portion extending outwardly from the pad portion) is tested. The test apparatus consists of two parts, which fit between the two jaws of an INSTRON® tensile tester and which are designed to draw apart. The upper part is in the form of an opensided cage, with a solid floor provided with a central ¾" hole. The lower part is a rod with a removable cap of 7/16" diameter. The rod moves in a vertical plane through the center of the hole in the cage. At the start of the test, a disc of the test sample, 1⅛" in diameter, is placed on the rod, pierced through its center and held in place by the cap. The rod is withdrawn through the hole and the force (in grams) is measured as the test sample is folded around the cap.

Light Occlusivity

Light occlusivity is measured using a Gardner Colorimeter Model XL-835 from Pacific Scientific Company, Bethesda, Md. using the method recommended by the manufacturer.

EXAMPLE 1

Porous Polyethylene Film was processed according to U.S. Pat. No. 4,539,256 with the modification of adding a blend of pigment masterbatches from C. B. Edwards Company, Minneapolis, Minn.

A 44:56 blend of high density polyethylene having a melt flow index of 0.07 (ASTM Condition E) available under the trade designation "GM 9255" from American Hoechst Company and mineral oil available under the trade designation Amoco White Mineral oil #31 USP grade (having a Brookfield Viscosity of 139 centipoise as per ASTM D 1824 Model LVT Spindle #1, 30 rpm, 22° C.) was extruded at the rate of 30 lb/hr using a twin screw extruded fitted with a film die having a gap sufficient to produce a 6 mil cast film. The polymer was extruded into a 27° C. water quench bath. The extrusion temperature was 221° C.

Thereafter, the film was solvent extracted with 1,1,1-trichloroelthane to remove the oil and biaxially stretched to 1.4 in the machine direction at 75° C. and 1.7 in the transverse direction at 77°–88° C.

The actual pigment loading in the film was 4.3% by weight and consisted of 0.86% black CBE-10478E, 1.72% yellow CBE-92113E and 1.72% red CBE-92114E. A skin tone film of 0.09 mm was produced and laminated in line to an adhesive transfer film prepared previously. The adhesive transfer film consisted of a solution cast 96:4 iso-octyl acrylate: acryamide copolymer prepared according to U.S. Pat. No. 2,884,126 (Reissue No. 24,906) on a Silicone release liner 2-8OBKG 157&168A from Daubert Chemical Co., Chicago, Ill. Coating weight was 0.45 grams per 200 cm². This adhesive-coated film was then laminated to a needled rayon web having a low density polyethylene film on one side (prepared according to U.S. Pat. No. 3,285,245) by placing the adhesive side of the pressure sensitive coated film against the non-film side of the needled web and laminating the two webs on a laboratory laminator with no heat and 200 g/cm force on a 30-cm Laminex machine (Rexham Co., Matthews, N.C.). This composite was die cut into the pad portion of the eye patch (FIG. 3) and affixed to a larger piece of Skin Tone Micropore tape (3M) die-cut to a similar shape. The porous polyethylene side of the pad was placed in contact with the adhesive side of the Micropore tape and pressed in place with moderate hand pressure. A liner 2-80-BKG-157 and 168A from Daubert Chemical Co. was applied to the adhesive side of the patch and covered the patch in two parts as illustrated in FIG. 2.

EXAMPLE 2

A second construction was also prepared using the pressure sensitive coated porous polyethylene film and needled web from Example 1. The needled web with film on one side was die-cut into the shape of the eye patch pad portion and the porous polyethylene pressure sensitive adhesive film was die-cut into a larger size of similar shape. The pad was then affixed to the adhesive-coated porous polyethylene film by placing the non film side of the pad against the adhesive side of the porous polyethylene film and applying moderate hand pressure. A liner was applied to the patch in the same manner as in Example 1.

Test results obtained with the eye patches of Examples 1 and 2 and some comparison test results obtained with eye patches of the prior art are given in Table 1.

TABLE I

| TEST SPECIMENS | MVT g/m²/24 hrs | CONFORMABILITY Grams | LIGHT OCCLUSIVITY % TRANSMISSION |
|---|---|---|---|
| Beiresdorf "Elastopad" | | | |
| Pad Area | 530 | 870 | <0.1 |
| Tape Area | 2920 | — | 76 |
| 3M Opticlude | | | |
| Pad Area | 926 | 735 | 24 |
| Tape Area | 3000 | — | 84 |
| Example 1 | | | |
| Pad Area | 926 | 550 | <0.1 |
| Tape Area | 3000 | — | 84 |
| Example 2 | | | |
| Pad Area | 928 | 360 | <0.1 |
| Tape Area | 1090 | — | 0.4 |

What is claimed is:

1. A self adherent eyepatch comprising:
   an absorbent pad shaped to fit over the eye having a nonadherent lower surface for contacting the eye and an opposing upper surface;
   a thin microporous polymeric film adhered to said upper surface of said absorbent pad and at least coextensive therewith, said film being capable of blocking at least 95 percent of the light of a preselected wavelength impinging thereon;
   pressure sensitive adhesive means extending around the periphery of said absorbent pad for adhering the eyepatch to the eye socket; and
   a removable protective liner covering said nonadherent lower surface of said absorbent pad and the exposed portion of said pressure sensitive adhesive;
   said eyepatch having a moisture vapor permeability of at least 600 grams per square meter per 24 hours throughout and a conformability value of less than 800 grams.

2. The eyepatch according to claim 1 wherein said film has a rim portion which extends beyond the periphery of said absorbent pad and said rim portion is coated on its under surface with said pressure sensitive adhesive.

3. The eye patch according to claim 1 wherein said pressure sensitive adhesive means is a tape applied over said film, and extending beyond the periphery of said film to attach the eyepatch to the eye socket.

4. The eyepatch according to claim 1 wherein said film is a microporous thermoplastic polymeric film.

5. The eyepatch according to claim 4 wherein said film comprises one or more pigments which render said film capable of blocking at least 95 percent of the light of a preselected wavelength impinging thereon.

6. The eyepatch according to claim 5 wherein said film is high density polyethylene.

7. The eyepatch according to claim 1 wherein said microporous film is skin-toned.

8. The eyepatch according to claim 1 wherein said absorbent pad is a nonwoven web of rayon fibers and said nonadherent surface is formed from polyethylene film heat bonded to said rayon fibers.

9. The eyepatch according to claim 3 wherein said tape comprises a breathable nonwoven backing.

10. The eyepatch according to claim 9 wherein said tape is skin-toned.

* * * * *

UNITED STATES PATENT AND TRADEMARK OFFICE
CERTIFICATE OF CORRECTION

PATENT NO. : 4,793,003

DATED : December 27, 1988            Page 1 of 2

INVENTOR(S) : John E. Riedel and Jay V. Ihlenfeld

It is certified that error appears in the above-identified patent and that said Letters Patent is hereby corrected as shown below:

Col. 1, line 25
    "ot" should be --to--.

Col. 2, line 9
    "no" should be --not--.

Col. 2, line 13
    "confortable" should be --comfortable--.

Col. 2, line 36
    "preferrably" should be --preferably--.

Col. 2, line 61
    "tramatized" should be --traumatized--.

Col. 2, line 67
    "appealling" should be --appealing--.

Col. 3, line 13
    "in" should be --an--.

UNITED STATES PATENT AND TRADEMARK OFFICE
CERTIFICATE OF CORRECTION

PATENT NO. : 4,793,003
DATED : December 27, 1988
INVENTOR(S) : John E. Riedel and Jay V. Ihlenfeld It is certified that error appears in the above-identified patent and that said Letters Patent is hereby corrected as shown below:

Col. 4, line 26
    "4,538,256" should be --4,539,256--.

Col. 4, line 44
    "pruposes" should be --purposes--.

Col. 5, line 31
    "alligned" should be --aligned--.

Col. 6, line 54
    "trichloroelthane" should be --trichloroethane--.

Col. 6, line 63
    "acryamide" should be --acrylamide--.

Signed and Sealed this

Ninth Day of May, 1989

Attest:

DONALD J. QUIGG

*Attesting Officer*      *Commissioner of Patents and Trademarks*